(12) United States Patent
Curtis

(10) Patent No.: US 7,368,888 B2
(45) Date of Patent: *May 6, 2008

(54) METHODS AND SYSTEMS FOR REDUCING UNINTENTIONAL COLLISIONS

(75) Inventor: Steven E. Curtis, Salt Lake City, UT (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/296,947

(22) Filed: Dec. 8, 2005

(65) Prior Publication Data

US 2006/0087274 A1    Apr. 27, 2006

Related U.S. Application Data

(62) Division of application No. 10/695,179, filed on Oct. 28, 2003, now Pat. No. 7,034,492.

(51) Int. Cl.
*G05B 11/42* (2006.01)

(52) U.S. Cl. .............. 318/610; 318/560; 318/623; 318/630

(58) Field of Classification Search .............. None
See application file for complete search history.

(56) References Cited

U.S. PATENT DOCUMENTS

| | | | |
|---|---|---|---|
| 3,696,282 A | 10/1972 | Hirokawa et al. |
| 4,211,927 A | 7/1980 | Hellstrom et al. |
| 4,345,194 A | 8/1982 | Green |
| 4,749,257 A | 6/1988 | Klausz |
| 4,893,068 A | 1/1990 | Evans, Jr. |
| 5,254,921 A | 10/1993 | Matsubara |
| 5,304,906 A | 4/1994 | Arita et al. |
| 5,710,496 A | 1/1998 | Boom |
| 5,723,965 A | 3/1998 | Yim |
| 5,973,467 A | 10/1999 | Eguchi |
| 6,088,633 A | 7/2000 | Yamamoto |
| 6,226,351 B1 | 5/2001 | Snoeren et al. |
| 6,298,283 B1 | 10/2001 | Kato et al. |
| 6,507,638 B2 | 1/2003 | Curtis et al. |
| 6,593,719 B2 | 7/2003 | Satta et al. |
| 6,594,339 B1 | 7/2003 | Alving et al. |
| 6,668,202 B2 | 12/2003 | Makino et al. |
| 6,686,990 B2 | 2/2004 | Hazelton et al. |
| 6,784,632 B2 | 8/2004 | Tomita |
| 7,034,492 B2 | 4/2006 | Curtis |

FOREIGN PATENT DOCUMENTS

EP    0 556 412    11/1997

OTHER PUBLICATIONS

EP Search Report, App. No. EP 04 25 6513 (Jan. 21, 2005).

*Primary Examiner*—Lincoln Donovan
*Assistant Examiner*—Erick Glass
(74) *Attorney, Agent, or Firm*—Armstrong Teasdale LLP

(57) ABSTRACT

A method for differentiating if a feedback signal is a result of an unintentional collision in a servo system includes injecting a feed forward term in the servo system.

9 Claims, 7 Drawing Sheets

METHODS AND SYSTEMS FOR REDUCING UNINTENTIONAL COLLISIONS

CROSS REFERENCE TO RELATED APPLICATIONS

This application is a Divisional Application of application Ser. No. 10/695,179 filed Oct. 28, 2003, now U.S. Pat. No. 7,034,492.

BACKGROUND OF THE INVENTION

This invention relates generally to imaging and, more particularly, to methods and systems for facilitating a reduction in unintentional collisions between an automatically moving structure and an object in proximity to the moving structure.

Moving devices that are used for medical diagnostic data gathering or therapeutic purposes are subject to collisions with obstructions, or with a patient or other object in proximity to the moving device. Movement is accomplished by a servo system (i.e., a digital/electrical/mechanical system that performs mechanical movement under software control, and that also uses feedback). Various means have been devised to abort motion when a collision-in-progress is occurring. These means include pressure and proximity sensors associated with bumpers or other targeted regions on the medical device, and collision sensing associated with feedback signals within the servo system of the device. Each type of sensing has important applications. The feedback sensing signals may provide more universal sensing capability than the use of pressure and proximity sensors because the feedback will indicate resistance to the directed motion that occurs anywhere along the moving structure. However, normal operation of the servo system can also create feedback signals that are not due to a collision but that are similar to a signal that a collision would induce. Additionally, the feed forward/feedback may be processed in a way that allows the system to inherently be less aggressive in powering motion against a collision, even before a collision is detected, while at the same time retaining the desired aggressiveness in powering motion resulting from an input control signal.

BRIEF DESCRIPTION OF THE INVENTION

In one aspect, a method for differentiating if a feedback signal is a result of an unintentional collision in a servo system is provided. The method includes injecting a feed forward term in the servo system.

In another aspect, a method of configuring a servo system with an initial aggressiveness level for responding to a collision and a desired aggressiveness level for responding to an input control signal is provided. The method includes reducing the initial aggressiveness level for responding to a collision, and maintaining the desired aggressiveness level for responding to the input.

In another aspect, an imaging system is provided. The imaging system includes a radiation source, a radiation detector positioned to receive radiation emitted by the source, a servo system configured to position at least one of the source, the detector, an object to be scanned, and a computer operationally coupled to the source, the detector, and the servo system. The computer is configured to inject a feed forward term in the servo system.

In yet another embodiment, a computer-readable medium encoded with a program is provided. The program is configured to instruct a computer to inject a feed forward term in a servo system.

DETAILED DESCRIPTION OF THE INVENTION

Herein described are methods and apparatus for facilitating the differentiation of whether a feedback signal in a servo system is the result of an legitimate operation (e.g., mechanical loading) or the result of an unintended collision.

Figure 1:
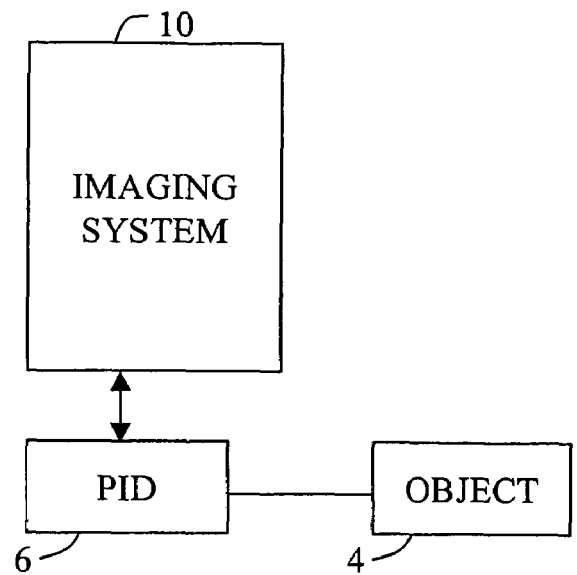
FIG. 1 illustrates an imaging system.

FIG. 1 illustrates an embodiment of an imaging system 10 in which the herein described apparatus and methods are implemented. Examples of imaging system 10 include an x-ray imaging system, an ultrasound imaging system, a magnetic resonance imaging (MRI) system, a single photon emission computed tomography (SPECT) imaging system, a computed tomography (CT) imaging system, and a positron emission tomography (PET) imaging system. Imaging system 10 scans an object 4, such as a heart, a liver, or a lung, and generates original projection data. In one embodiment imaging system includes a Physiological information device (PID) 6 coupled to object 4. An example of PID 6 includes an electrocardiograph that generates an electrocardiogram (EKG). PID 6 generates physiological cycle signals, such as EKG signals or respiratory signals, including a plurality of phases, such as cardiac phases or respiratory cycle phases.

Figure 2:
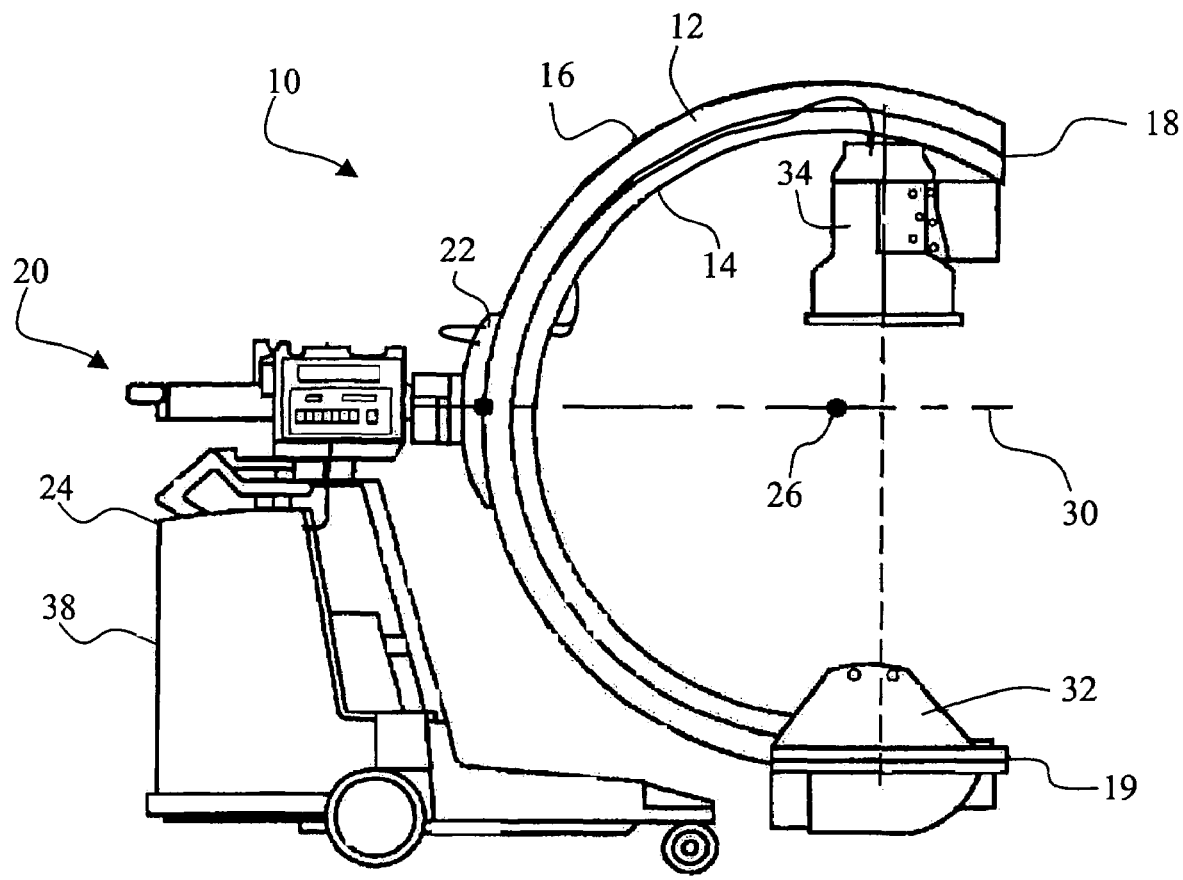
FIG. 2 illustrates a mobile C-arm X-ray system.

In an exemplary embodiment, and as illustrated in FIG. 2, imaging system 10 is a mobile C-arm X-ray system 10. System 10 includes a C-arm 12 having inner and outer circumferences 14 and 16, respectively, and terminating in opposing upper and lower distal ends 18 and 19. C-arm 12, in the exemplary embodiment has a uniformly circular C-shape, but may alternatively include any arc-shaped member.

C-arm 12 is held in a suspended position by support means such as structure, generally designated at 20, which includes a support arm 22 mounted upon a wheeled base 24. Support arm 22 provides for rotational movement of C-arm 12 about an axis of lateral rotation 30, either by a bearing assembly between support arm 22 and C-arm 12, or by support 22 itself being rotatably mounted with respect to base 24.

Wheeled base 24 enables transport of C-arm 12 from a first location to a second location. As such, the wheels of the base operate as transporting means coupled to support structure 20 for transporting support arm 22 and C-arm 12 from a first location to a second location because it may be desirable to move X-ray equipment from one room to another. The mobile nature of the apparatus 10 as provided by the wheeled base 24 offers increased access by patients in many different rooms of a hospital, for example.

Support arm 22 is slidably mounted to the outer circumference 16 of C-arm 12 and support structure 20 includes structure and mechanisms necessary to enable selective, sliding orbital motion of C-arm 12 about an axis of orbital rotation 26 to a selected position. Axis 26 coincides with a center of curvature of C-arm 12 and with axis of lateral rotation 30. It will be appreciated that the sliding orbital motion causes the C-arm 12 to move through various sliding points of attachment 28 to the support arm 22. The support structure 20 further includes mechanisms for laterally rotating the support arm 22 selectable amounts about axis of lateral rotation 30 to a selected lateral position. The combination of sliding orbital motion and lateral rotation enables manipulation of C-arm 12 in two degrees of freedom, i.e. about two perpendicular axes. This provides a kind of spherical quality to the movability of C-arm 12 (e.g., the sliding orbital motion and lateral rotation enable an X-ray source 32 coupled to C-arm 12 to be moved to substantially any latitude/longitude point on a lower hemisphere of an imaginary sphere about which C-arm 12 is moveable).

System 10 includes an X-ray source 32 and an image receptor 34 as known generally in the X-ray diagnostic art, mounted upon opposing locations, respectively, on C-arm 12. X-ray source 32 and image receptor 34 may be referred to collectively as the X-ray source/image receptor 32/34. Image receptor 34 can be an image intensifier or the like. The orbital and laterally rotational manipulation of C-arm 12 enables selective positioning of X-ray source/image receptor 32/34 with respect to the width and length of a patient located within an interior free space 36 of C-arm 12. More specifically, system 10 includes a servo system (i.e., a digital/electrical/mechanical system that performs mechanical movement under software control, and that also uses feedback) coupled to a computer 38. The sliding orbital movement of C-arm 12 causes the X-ray source/image receptor 32/34 to move along respective arcuate movement paths. Image receptor 34 is, in one embodiment, secured to inner circumference 14 of C-arm 12 and X-ray source 32 may also be secured to inner circumference 14.

As used herein, an element or step recited in the singular and preceded with the word "a" or "an" should be understood as not excluding plural the elements or steps, unless such exclusion is explicitly recited. Furthermore, references to "one embodiment" of the present invention are not intended to be interpreted as excluding the existence of additional embodiments that also incorporate the recited features.

In one embodiment, computer 38 includes a device (not shown), for example, a floppy disk drive or CD-ROM drive, for reading instructions and/or data from a computer-readable medium, such as a floppy disk or CD-ROM. In another embodiment, computer 38 executes instructions stored in firmware (not shown). Computer 38 is programmed to perform functions described herein, and as used herein, the term computer is not limited to just those integrated circuits referred to in the art as computers, but broadly refers to processors, microcontrollers, microcomputers, programmable logic controllers, application specific integrated circuits, and other programmable circuits, and these terms are used interchangeably herein.

Although the specific embodiment mentioned above refers to a mobile C-arm x-ray apparatus, the herein described methods equally apply to all other imaging modalities, as well as any application utilizing servos around objects which it is desirable not to collide with.

Additionally, although the herein described methods are described in a medical setting, it is contemplated that the benefits of the methods accrue to non-medical imaging systems such as those systems typically employed in an industrial setting or a transportation setting, such as, for example, but not limited to, a baggage scanning system for an airport, other transportation centers, government buildings, office buildings, and the like. The benefits also accrue to micro x-ray, PET, and CT systems which are sized to study lab animals as opposed to humans.

Figure 3:
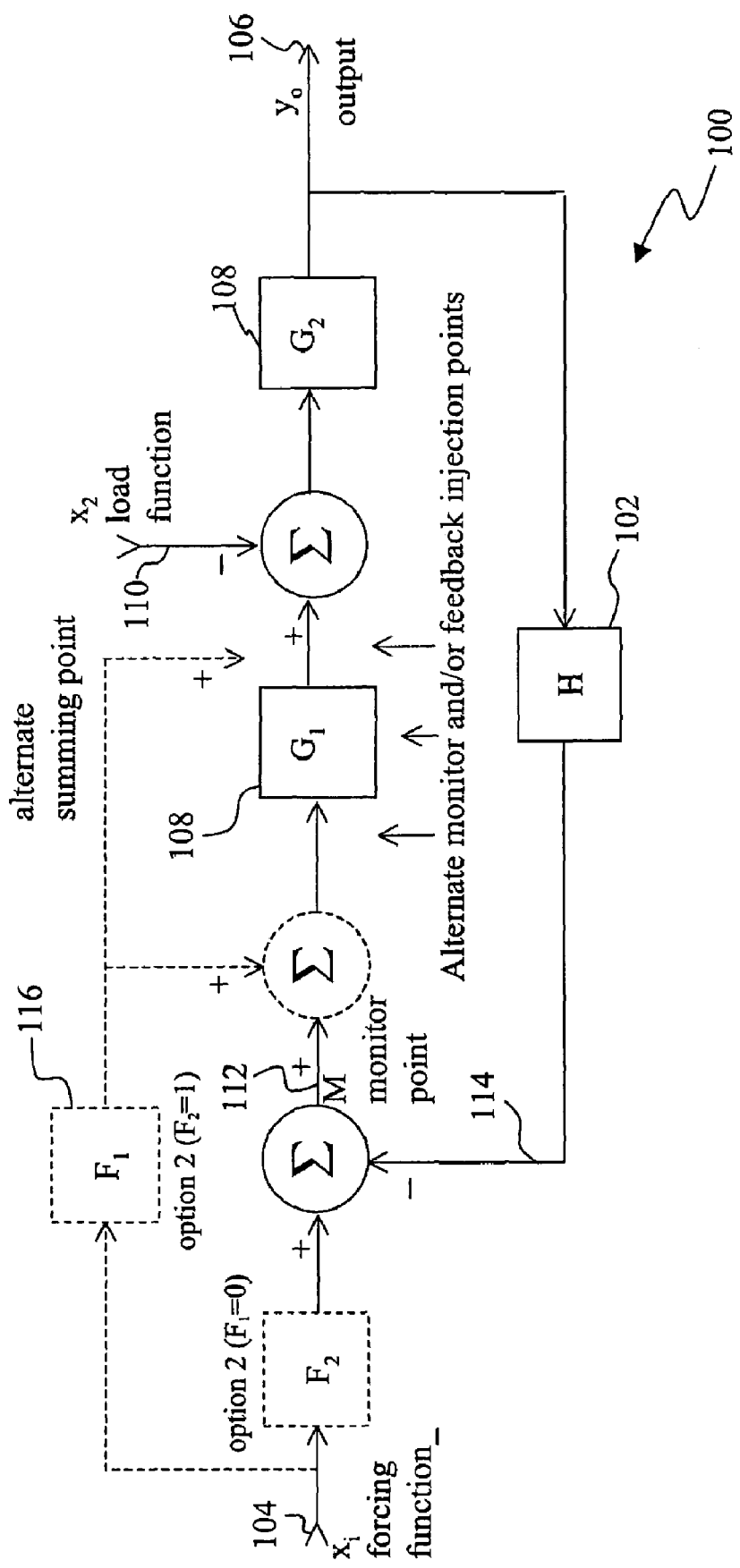
FIG. 3 illustrates a servo system.

The herein described methods and apparatus use feed forward to enhance the detection of an unwanted collision between an electromechanical motion system and some obstacle in the path of the intended motion. Additionally, the method allows optimization of feed forward and feedback in such a way that allows the system to inherently be less aggressive in powering motion against a collision, even before a collision is detected, while at the same time retaining the desired aggressiveness in powering motion resulting from an input control signal (forcing function). FIG. 3 illustrates a servo system 100 including a feedback mechanism 102 (block H) that receives information about motion or position, and converts the information into a signal that can be subtracted from an input forcing function $x_i$ 104. $x_i$ forcing function 104 is the control signal or digital command that directs the entire servo system to respond, such that a mechanical output $y_o$ 106 moves in an intended way. A plurality of blocks 108 ($G_1$ and $G_2$) represent various parts of the servo system structure such as data processed in a computer, an electrical motor, and a mechanism that converts rotation of the motor shaft into a useful motion or position of the device. A signal $X_2$ represents a load function 110, e.g., a parameter such as friction or other mechanical loading that tends to resist movement driven by a motor shaft. A monitor point 112 (M) provides data to the system that represents the difference between $x_i$ forcing function 104 and a feedback signal 114 that has passed through H feedback block 102. The value of M is generally small (depending on the many parameters that define servo system 100). However, M may temporarily have larger values when servo system 100 is being subjected to certain types of stimulus transients that are applied to either $x_1$ or $x_2$. By proper interpretation of M, it is possible to determine if servo system 100 has encountered a (undesired) collision-in-progress. Under this condition servo system 100 performance can be altered to avoid the unwanted result of a collision from a fully executed movement. Feed forward through a block $F_1$ 116 allows special processing of the $x_i$ forcing function to achieve an enhanced detectability to collisions at M 112. Note that $F_1$ could be summed into the system at points other than that shown in FIG. 3, with variations in the results. Also, monitor point M 112 can be placed at locations other than that shown in FIG. 3, with variations in the results. Also, multiple points for injecting feedback (114) could be used, in addition to those points shown in FIG. 3. Depending on characteristics of any system, the placement of feed forward injection, the monitoring point, and feedback may vary.

One can consider the various parts of servo system 100 illustrated in FIG. 3 as being represented in the Laplace domain. Then, treating the two inputs $x_i$ and $x_2$ separately by superposition, and by using Mason's law, one obtains $$\frac{y_0}{x_i} = \frac{(F_1+1)G_1G_2}{1+G_1G_2H}, \quad \text{1A)}$$

$$\frac{y_0}{-x_2} = \frac{G_2}{1+G_1G_2H} \quad \text{1B)}$$

$G_1$ can be chosen to make $y_o/x_2$ behave optimally for collision detection and avoidance. An alternative version of $G_1$ is selected and defined as $G_1'$, which is chosen to make $y_o/x_i$ behave optimally from the point of view of the forcing function $x_i$ but without using feed forward ($F_1=0$). Finally, using $G_1$ and $F_1$ (but not $G_1'$), require a transfer function for $y_o/x_i$ that behaves identically to the prior $y_o/x_i$, and solve for the required $F_1$ to force this result. The following equations show this process.

$$\frac{(F_1+1)G_1G_2}{1+G_1G_2H} = \frac{G_1'G_2}{1+G_1'G_2H} \quad \text{2)}$$

Solving for $F_1$:

$$F_1 = \frac{G_1'(1+G_1G_2H) - G_1(1+G_1'G_2H)}{G_1(1+G_1'G_2H)} \quad \text{3)}$$

Thus, using a feed forward term $F_1$ in the servo system enables it to be optimized for both $y_o/x_i$ and $y_o/x_2$, such that collision detection monitoring at M is enhanced without compromising responsiveness to the forcing function $x_i$. Additionally injecting a feed forward term to optimize $y_o/x_i$ allows for the separate and independent optimizing of $y_o/x_2$ via the standard existing loop parameters without the influence of feed forward.

Figure 4:
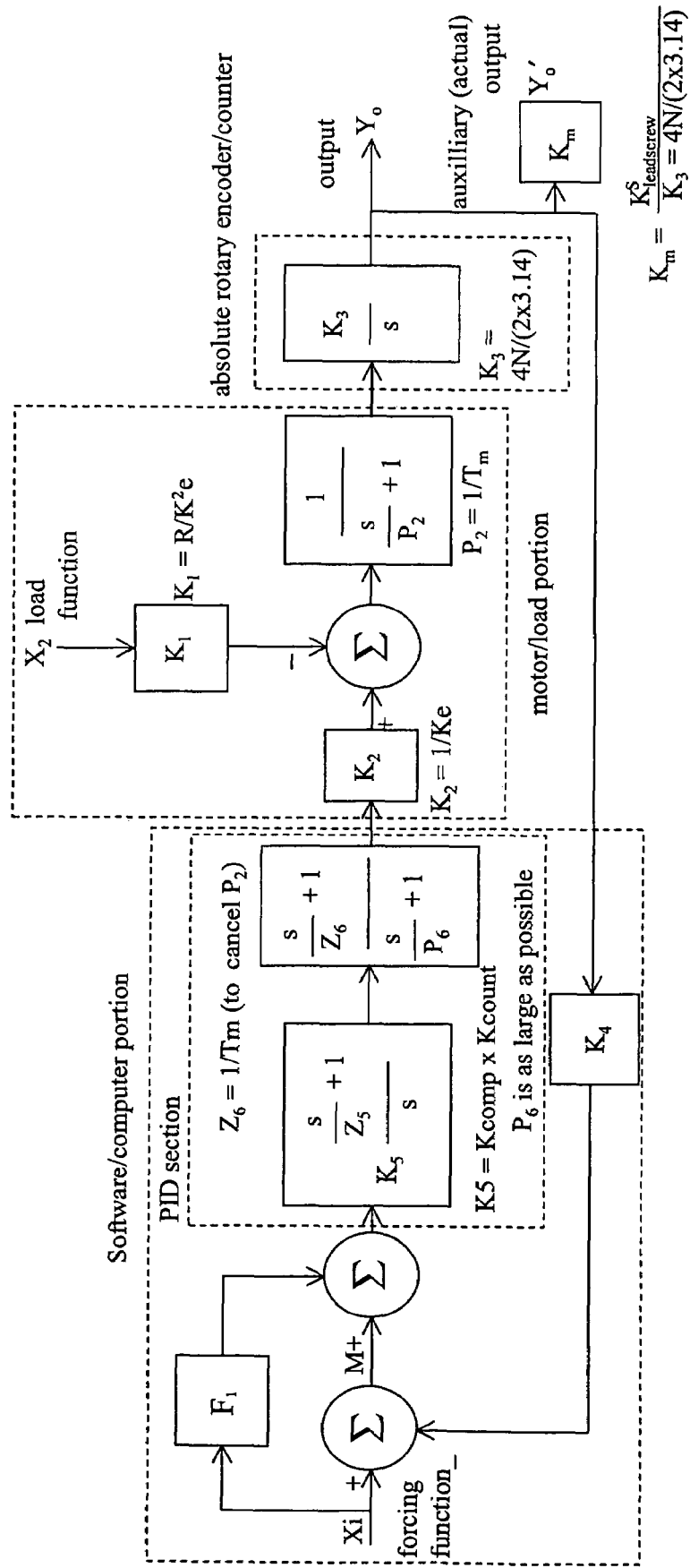
FIG. 4 illustrates a specific example of an electromechanical servos system shown more generically in FIG. 3.

FIG. 4 illustrates a specific example of an electromechanical servos system shown generically in FIG. 3. The closed loop response for FIG. 4 inputs $x_i$ and $x_2$ are given $$y_0 = x_i \frac{(F+1)\frac{K_2K_3K_5}{Z_5Z_6}s^2 + (F+1)\left(\frac{1}{Z_5}+\frac{1}{Z_6}\right)K_2K_3K_5s + (F+1)K_2K_3K_5}{\frac{1}{P_2P_6}s^4 + \left(\frac{1}{P_2}+\frac{1}{P_6}\right)s^3 + \left(\frac{K_2K_3K_4K_5}{Z_5Z_6}+1\right)s^2 + \left(\frac{1}{Z_5}+\frac{1}{Z_6}\right)K_2K_3K_4K_5s + K_2K_3K_4K_5} -$$

$$x_2 \frac{\frac{K_1K_3}{P_6}s^2 + K_1K_3s}{\frac{1}{P_2P_6}s^4 + \left(\frac{1}{P_2}+\frac{1}{P_6}\right)s^3 + \left(\frac{K_2K_3K_4K_5}{Z_5Z_6}+1\right)s^2 + \left(\frac{1}{Z_5}+\frac{1}{Z_6}\right)K_2K_3K_4K_5s + K_2K_3K_4K_5}$$

Next, for $y_o/x_i$ preferred terms $K'_5$ and $Z'_5$ are selected instead of $K_5$ and $Z_5$. With no feed forward (F=0) this result in:

$$\frac{y_0}{x_i} = \frac{\frac{K_2K_3K'_5}{Z'_5Z_6}s^2 + \left(\frac{K'_5}{Z'_5}+\frac{K'_5}{Z_6}\right)K_2K_3s + K_2K_3K'_5}{\frac{1}{P_2P_6}s^4 + \left(\frac{1}{P_2}+\frac{1}{P_6}\right)s^3 + \left(\frac{K_2K_3K_4K'_5}{Z'_5Z_6}+1\right)s^2 + \left(\frac{1}{Z'_5}+\frac{1}{Z_6}\right)K_2K_3K_4K'_5s + K_2K_3K_4K'_5} \quad \text{5)}$$

From inspection of FIG. 4 it is clear that $$M = x_i - y_0K_4 \quad \text{6)}$$

F can be determined using equation 3) to obtain equation 7).

$$F = \frac{K'_5 \frac{\frac{s}{Z'_5}+1}{s} \times \frac{\frac{s}{Z_6}+1}{\frac{s}{P_6}+1} \times K_2 \times \left(1 + K_5 \times \frac{\frac{s}{Z_5}+1}{s} \times \frac{\frac{s}{Z_6}+1}{\frac{s}{P_6}+1} \times K_2 \times \frac{1}{\frac{s}{P_2}+1} \times \frac{K_3}{s} \times K_4\right) -}{K_5 \times \frac{\frac{s}{Z_5}+1}{s} \times \frac{\frac{s}{Z_6}+1}{\frac{s}{P_6}+1} \times K_2 \times \left(1 + K'_5 \times \frac{\frac{s}{Z'_5}+1}{s} \times \frac{\frac{s}{Z_6}+1}{\frac{s}{P_6}+1} \times K_2 \times \frac{1}{\frac{s}{P_2}+1} \times \frac{K_3}{s} \times K_4\right)}$$

$$\frac{K_5 \times \frac{\frac{s}{Z_5}+1}{s} \times \frac{\frac{s}{Z_6}+1}{\frac{s}{P_6}+1} \times K_2 \times \left(1 + K'_5 \times \frac{\frac{s}{Z'_5}+1}{s} \times \frac{\frac{s}{Z_6}+1}{\frac{s}{P_6}+1} \times K_2 \times \frac{1}{\frac{s}{P_2}+1} \times \frac{K_3}{s} \times K_4\right)}{} \quad \text{7)}$$

Rearranging equation 7), one obtains 8)

$$F = \frac{\left(\frac{K_2K_5'}{Z_5'Z_6}s^2 + \left(\frac{1}{Z_5'} + \frac{1}{Z_6}\right)K_2K_5's + K_2K_5'\right)\left(\frac{1}{P_2P_6}s^4 + \left(\frac{1}{P_2} + \frac{1}{P_6}\right)s^3 + \left(\frac{K_2K_3K_4K_5}{Z_5Z_6} + 1\right)s^2 + \left(\frac{1}{Z_5} + \frac{1}{Z_6}\right)K_2K_3K_4K_5s + K_2K_3K_4K_5\right) -}{\left(\frac{K_2K_5}{Z_5Z_6}s^2 + \left(\frac{1}{Z_5} + \frac{1}{Z_6}\right)K_2K_5s + K_2K_5\right)\left(\frac{1}{P_2P_6}s^4 + \left(\frac{1}{P_2} + \frac{1}{P_6}\right)s^3 + \left(\frac{K_2K_3K_4K_5'}{Z_5'Z_6} + 1\right)s^2 + \left(\frac{1}{Z_5'} + \frac{1}{Z_6}\right)K_2K_3K_4K_5's + K_2K_3K_4K_5'\right)}$$

$$\frac{\left(\frac{K_2K_5}{Z_5Z_6}s^2 + \left(\frac{1}{Z_5} + \frac{1}{Z_6}\right)K_2K_5s + K_2K_5\right)\left(\frac{1}{P_2P_6}s^4 + \left(\frac{1}{P_2} + \frac{1}{P_6}\right)s^3 + \left(\frac{K_2K_3K_4K_5'}{Z_5'Z_6} + 1\right)s^2 + \left(\frac{1}{Z_5'} + \frac{1}{Z_6}\right)K_2K_3K_4K_5's + K_2K_3K_4K_5'\right)}{}$$ 8)

For simplification, a change of notation is used, referencing equation 8).

$$F = \frac{(As^2 + Bs + C)(Ds^4 + Es^3 + Ps^2 + Gs + H) -}{(Is^2 + Js + K)(Ds^4 + Es^3 + Ls^2 + Ms + N)}$$

$$\frac{(Is^2 + Js + K)(Ds^4 + Es^3 + Ls^2 + Ms + N)}{(Is^2 + Js + K)(Ds^4 + Es^3 + Ls^2 + Ms + N)}$$ 9)

Finally, $$F = \frac{\begin{array}{l}(AD - ID)s^6 + (AE + BD - IE - JD)s^5 + (AP + BE + CD - \\ IL - JE - KD)s^4 + (AG + BP + CE - IM - JL - KE)s^3 + \\ (AH + BG + CP - IN - JM - KL)s^2 + (BH + CG - JN - KM)s + \\ CH - KN\end{array}}{\begin{array}{l}IDs^6 + (IE + JD)s^5 + (IL + JE + KD)s^4 + \\ (IM + JL + KE)s^3 + (IN + JM + KL)s^2 + (JN + KM)s + KN\end{array}}$$ 10)

Figure 5:
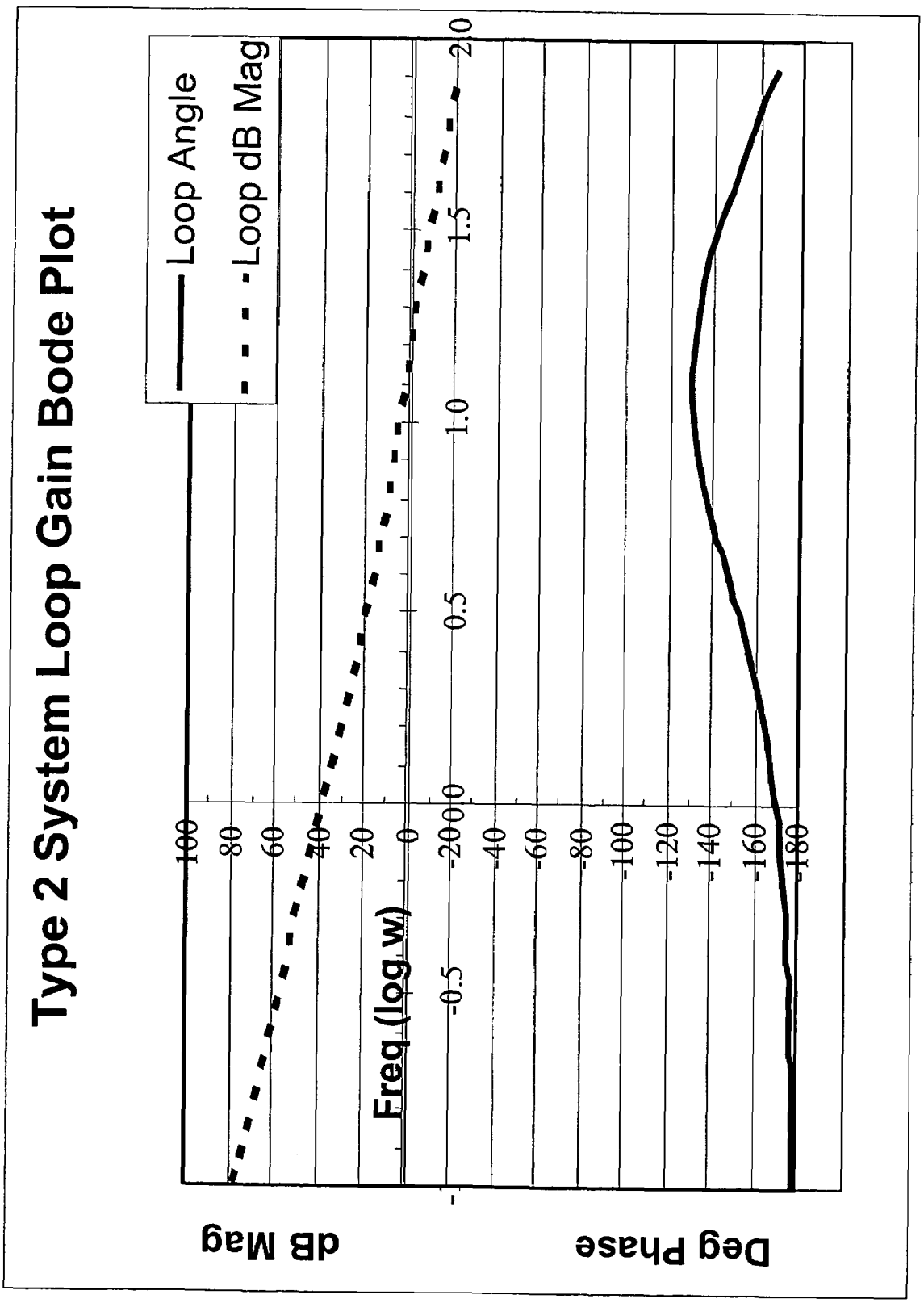
FIG. 5 illustrates a virtual loop gain Bode plot for $x_i$.

For the example application, the loop gain Bode plot that is optimized for $x_i$ is given in FIG. 5 with associated optimized parameters listed in Table 1. Note, the loop gain Bode plot in FIG. 5 was optimized for $x_i$ using $K_5'$ and $Z_5'$. Because of the feed forward parameter F (equation 10), this plot's phase margin can be used to predict the transient response of $y_o/x_i$. Note that for true stability, a Bode plot using $K_5$ and $Z_5$ (not $K_5'$ and $Z_5'$) can be used.

TABLE 1

| System Parameters | Servo Inputs | Calculations | |
|---|---|---|---|
| Kcomp = | 0.07 | Tm = | 0.086 |
| K4 = | 1 | K5' = | 0.006020 |
| Z5' = | 5 | P2 = | 11.655 |
| Tsample period = | 0.002 | Z6 = | 11.656 |
| Tcomp time = | 0.002 | K2 = | 41.841 |
| w start = | 0.1 | K1 = | 2626.004 |
| Scale Factor = | 1.2 | K3 = | 318.310 |
| Quad Enc Slits = | 500 | Km = | 1.000 |
| R = | 1.5 | Kloop@1r = | 80.177 |
| Ke = | 0.0239 | | |
| J = | 3.27E−05 | | |
| Kcount = | 0.086 | | |
| Kleadscrew = | 318.31 | | |

Figure 6:
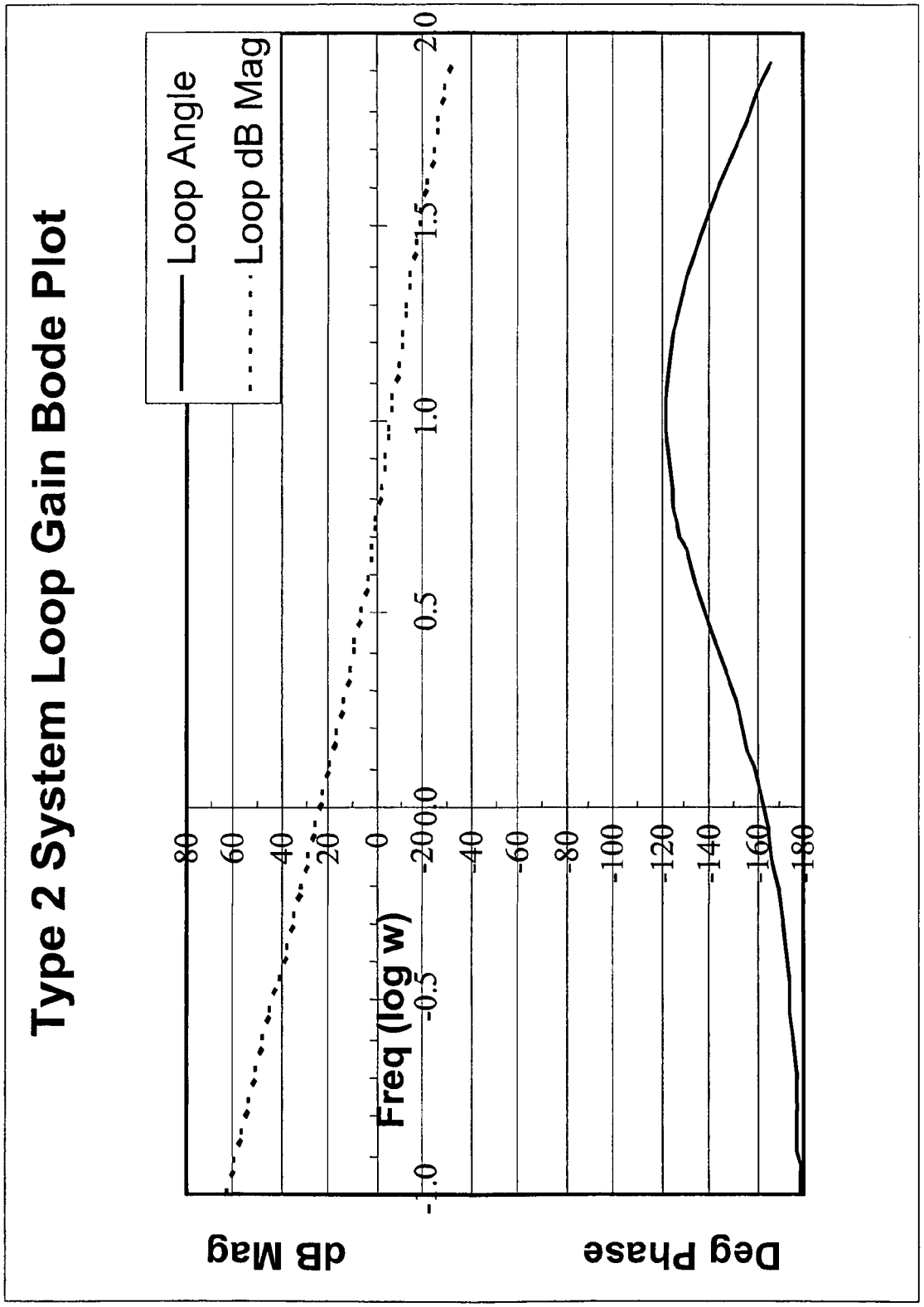
FIG. 6 illustrates a loop gain Bode plot for $x_2$.

The loop gain Bode plot that is optimized for $x_2$ is given in FIG. 6 with associated optimized parameters listed in Table 2. The plot was optimized for $x_2$ using $K_5$ and $Z_5$. Note, the plots margins can be used to predict the transient response of $y_o/x_2$.

TABLE 2

| System Parameters | Servo Inputs | Calculations | |
|---|---|---|---|
| Kcomp = | 0.01395 | Tm = | 0.086 |
| K4 = | 1 | K5 = | 0.001200 |
| Z5 = | 3 | P2 = | 11.655 |
| Tsample period = | 0.002 | Z6 = | 11.656 |
| Tcomp time = | 0.002 | K2 = | 41.841 |
| w start = | 0.1 | K1 = | 2626.004 |
| Scale Factor = | 1.2 | K3 = | 318.310 |
| Quad Enc Slits = | 500 | Km = | 1.000 |
| R = | 1.5 | Kloop@1r = | 15.978 |
| Ke = | 0.0239 | | |
| J = | 3.27E−05 | | |
| Kcount = | 0.086 | | |
| Kleadscrew = | 318.31 | | |

For an actual system represented by the example application, some blocks of FIG. 4 (including the F term given in equation 10) could be implemented in a computer and those functions accomplished via software programming using z-transforms of the Laplace equations. Other parts of the system can be realized in the form of electronic circuitry, an electric motor, and mechanical drive parts and other physical mechanisms. By proper use of equations 4), 5), and 6) a simulation of responses for the example application can be obtained, as though the feed forward term defined in equation 10) had been applied to an actual servo system.

Figure 7:
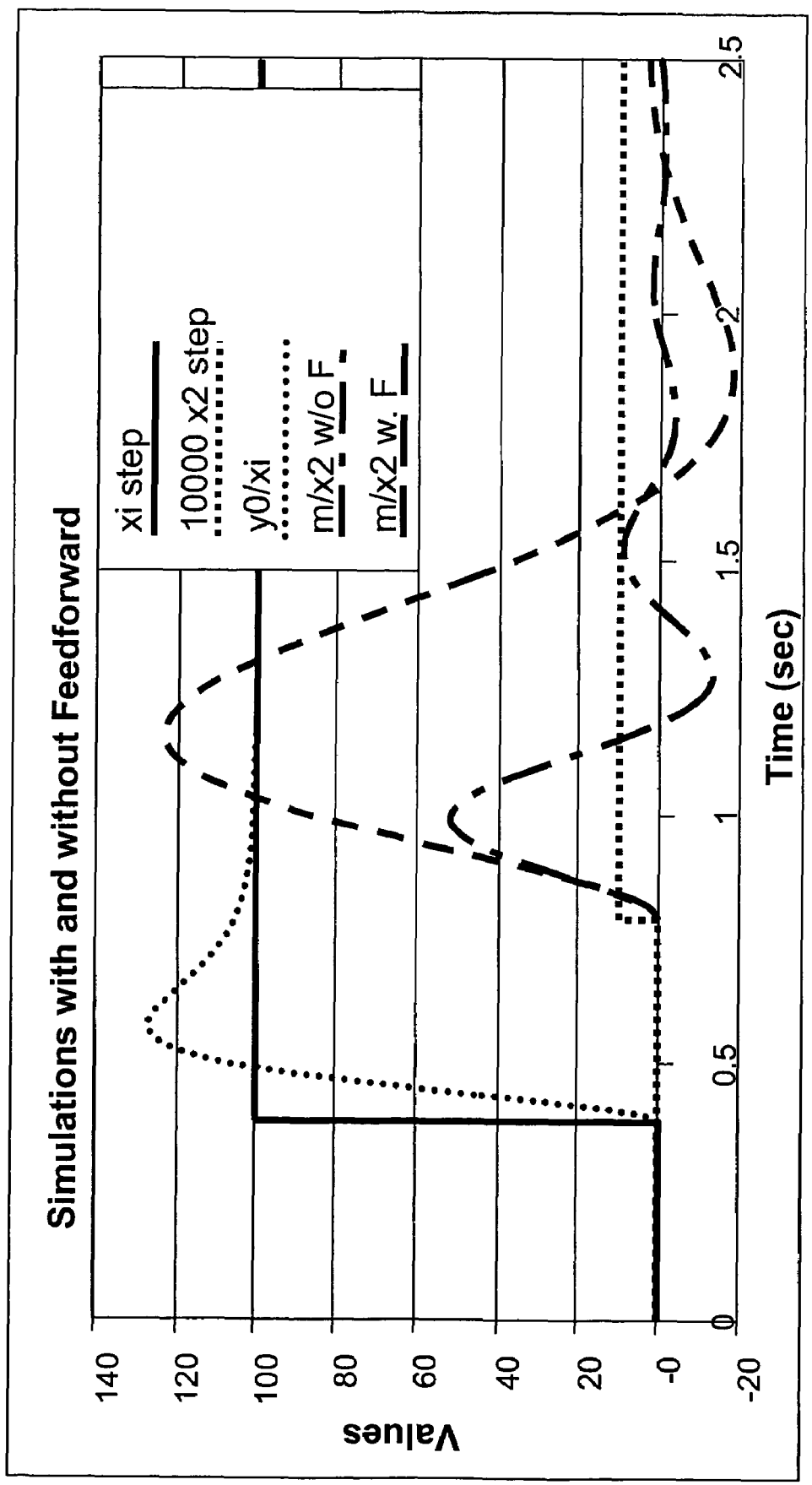
FIG. 7 illustrates a simulated response output for $y_o$ from a step input $x_i$ (forcing function to command the mechanism to move), and for $y_0$ from a step input $x_2$ (collision signal) with and without feed forward.

In FIG. 7 the simulated response output, $y_o$, is shown for a step response input from $x_i$ (forcing function to command the mechanism to move) for the topology of FIG. 4. Also shown in FIG. 7 are the monitor point signals, M, for a step at $x_2$ (representing a collision) that would occur with and without using feed forward. The peak M monitor signal is larger when feed forward is applied, having a ratio of about 2.4. Note, the collision step is amplified in the plot so it can be seen, due to the units used in FIG. 7. Because the example system uses a feedback constant of 1 (that is, $K_4$=1), note that the output $y_o$ is equivalent in magnitude to M (differing only by having an opposite polarity). Therefore, the plot for $M/x_2$ also represents the plot for $y_o/x_2$ (except for polarity). It is noted that $M/x_2$ with feed forward changes more quickly than $M/x_2$ without feed forward. This indicates that $y_o$ would also change more quickly, and that $y_o$ would therefore be more responsive to the collision signal $x_2$. With proper use of feed forward, the servo system would therefore not be as aggressive in powering motion through the collision, even before the M monitor point signal has been processed as a means to detect collision (and initiate a command to stop motion).

Figure 8:
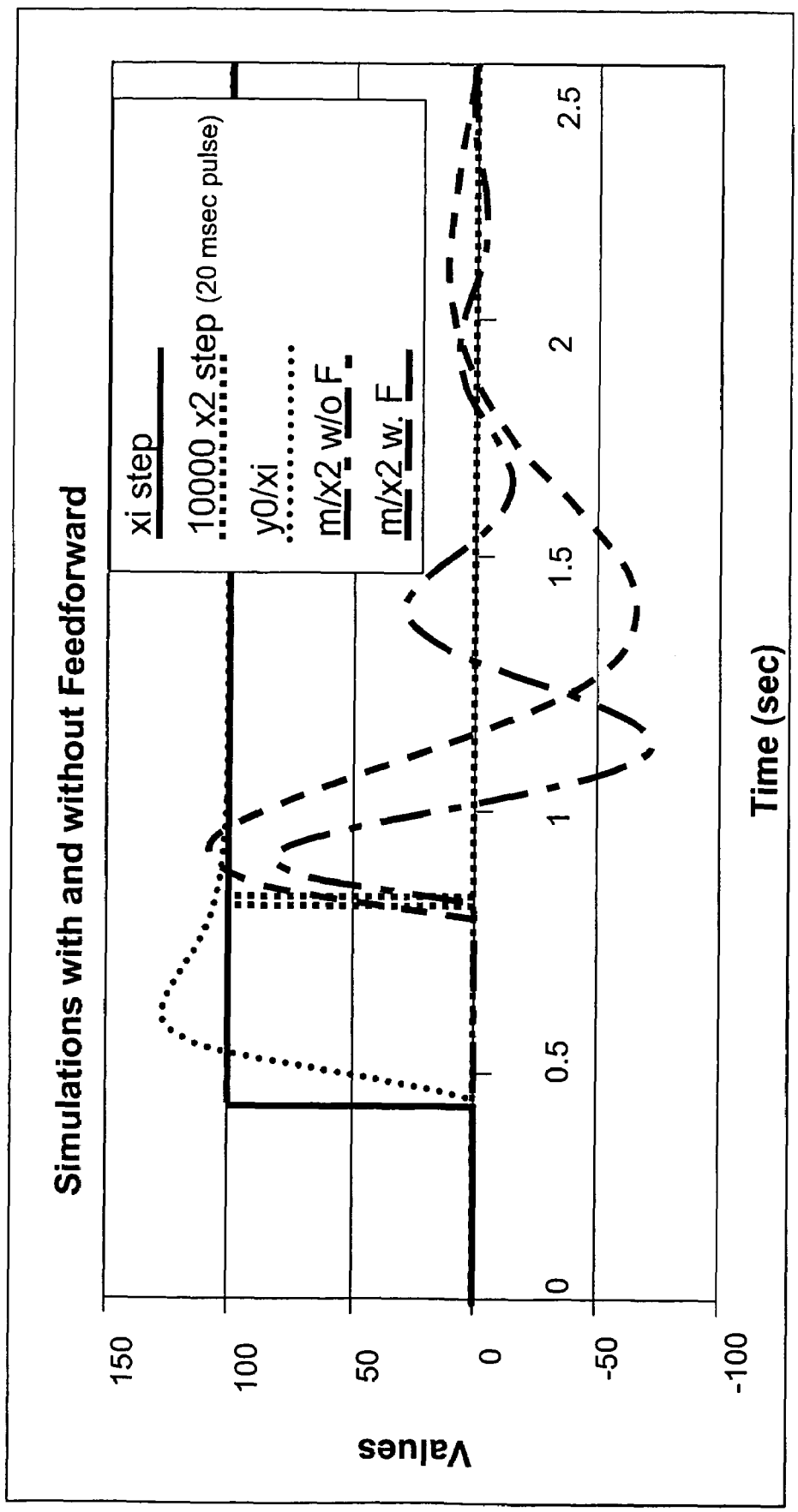
FIG. 8 illustrates a simulated response output for $y_o$ from a step input $x_i$, and for $y_0$ from a pulse input $x_2$ with and without feed forward.

In FIG. 8 the simulated response output, $y_o$, is shown for a step response input from $x_i$, and is identical to the simulation for $y_o$ shown in FIG. 7. Also shown in FIG. 8 are the monitor point signals, M, that would occur with and without using feed forward for a 20 msec pulse at $x_2$ (representing a bump that might occur when an imperfect mechanism is in motion). In this case the ratio for the peak M monitor signal with and without feed forward is about 1.4. Note, the pulse is amplified in the plot so it can be seen, due to the units used in FIG. 8.

The ratio of the simulated ratios with/without feed forward is 2.4/1.4=1.7. This means that the example servo system, when stimulated as described, can detect a smaller legitimate collision without also being subject to false alarms from a bump due to an imperfect mechanism. Therefore one technical effect is the enhanced sensitivity to collision stimulus. Because of the enhanced sensitivity to collision stimulus, the detection threshold at M could be increased. Then the servo system is less likely to generate a false alarm from a monitor signal that results from the $x_i$ forcing function.

While the invention has been described in terms of various specific embodiments, those skilled in the art will recognize that the invention can be practiced with modification within the spirit and scope of the claims.

What is claimed is:

1. A method of operating a servo system having an initial level of output for responding to a collision and a predetermined first level of output for responding to an input control signal, said method comprising:
    reducing the initial level of output to a second level of output for responding to the collision; and
    maintaining the first level of output using an input control signal feed forward that forces a mechanical output of the system to equal the first level of output when the feed forward equals zero and when not reducing the initial level of output.

2. A method in accordance with claim 1 further comprising optimizing a transfer function yo/x2, wherein yo is a signal representative of the mechanical output of the system and x2 is a load function.

3. A method in accordance with claim 2 wherein said feed forward dependent upon the forcing function is selected to optimize the transfer function.

4. A method in accordance with claim 2 wherein said optimizing a transfer function further comprises optimizing the transfer function without the influence of the feed forward.

5. A method in accordance with claim 1 further comprising initiating a command to stop movement when a collision is detected.

6. A method of operating a servo system having an initial level of output for responding to a collision and a predetermined first level of output for responding to an input control signal, said method comprising:
    reducing the initial level of output to a second level of output for responding to the collision; and
    maintaining the first level of output using an input control signal feed forward that increases the first level of output to a third level of output, the third level of output equal to a level of output with the feed forward removed and with the initial level of output lowered for response to a collision.

7. A method in accordance with claim 6 wherein the servo system includes a feedback system, said reducing the initial level of output further comprises reducing the initial level of output by optimizing a feedback system for collisions.

8. A method in accordance with claim 6 wherein said maintaining the first level of output further comprises maintaining the first level of output by providing a feed forward term to the servo system.

9. A method in accordance with claim 8 wherein said feed forward term is injected into a plurality of points in the servo system.

* * * * *